United States Patent
Kühnle et al.

(10) Patent No.: US 6,410,796 B2
(45) Date of Patent: Jun. 25, 2002

(54) PROCESS FOR THE PREPARATION OF POLY(FLUOROALKYL)ACETOPHENONES

(75) Inventors: Wulf Kühnle; Thomas Höpfner, both of Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/732,684

(22) Filed: Dec. 8, 2000

(30) Foreign Application Priority Data

Dec. 22, 1999 (DE) .......................................... 199 62 011
Jan. 27, 2000 (DE) .......................................... 100 03 321

(51) Int. Cl.$^7$ .............................................. C07C 45/00
(52) U.S. Cl. ....................................................... 568/323
(58) Field of Search .......................................... 568/323

(56) References Cited

FOREIGN PATENT DOCUMENTS

| DE | 197 19 054 | 11/1998 |
| EP | 0 949 243 | 10/1999 |

OTHER PUBLICATIONS

Tetrahedron Letters, No. 53, (month unavailable) 1970, pp. 4647–4650, G. H. Posner and C.E. Whitten, Methyl and n–Alkyl Ketones from Carboxylic Acid Chlorides and Organocopper Reagents.

"Method for Preparation of Acetophenone Derivatives" Research Disclosure, Kenneth Mason Publications, Hampshire, GB, Nr. 402, 1. Oktober 1997 (Oct. 1, 1997), Seite 706 XP000726840 ISSN: 0374–4353 *Seite 706*.

*Primary Examiner*—Alan Siegel
(74) *Attorney, Agent, or Firm*—Joseph C. Gil; Richard E. L. Henderson

(57) ABSTRACT

Acetophenones which are di- or polysubstituted by fluoroalkyl groups on the aromatic ring are prepared in a particularly advantageous manner from the corresponding fluoroalkylanilines and acetaldoxime by preparing a corresponding diazonium salt mixture from the fluoroalkylaniline, reacting this mixture with acetaldoxime in the presence of at least one copper and/or palladium compound, without adding buffer salts or a reducing agent, carrying out the reaction with acetaldoxime at 5 to 50° C. and in the presence of halide ions and at least one strong acid that is not a hydrohalic acid, and finally heating the mixture to a temperature in the range 70 to 160° C.

12 Claims, No Drawings

PROCESS FOR THE PREPARATION OF POLY(FLUOROALKYL)ACETOPHENONES

BACKGROUND OF THE INVENTION

The present invention relates to an improved process for the preparation of acetophenones that are substituted by two or more fluoroalkyl groups on the aromatic ring. Such compounds are useful intermediates for the preparation of active ingredients for the treatment of inflammation, migraines, vomiting, and pain. In particular, the present invention relates to a process for the preparation of bis-3, 5-(trifluoromethyl) acetophenone.

It is known that bis-3,5-(trifluoromethyl)acetophenone can be prepared from bis-3,5-(trifluoromethyl)benzoyl chloride by reaction with organic copper compounds (*Tetrahedron Letters*, No. 53, 4647-50 (1970)). A disadvantage of this process is the required preparation and use of lithium dialkylcopper compounds at −78° C. and with the absolute exclusion of water. Such methods can be used in the laboratory, but not on an industrial scale.

As a process for the preparation of bis-3,5-(trifluoromethyl)acetophenone, it is known to prepare the corresponding diazonium salt mixture from fluoroalkylaniline and sodium nitrite in the presence of sulfuric acid, then to add the mixture, at −5 to ±0° C., to an initial charge that comprises water, acetaldoxime, a copper(II) salt, possibly a reducing agent (sodium thiosulfate), and in every case a large amount of sodium acetate buffer. For work-up, hydrochloric acid is added, the mixture is refluxed, steam distillation or phase separation is carried out, and the mixture is distilled under reduced pressure. This gives bis-3,5-(trifluoromethyl)acetophenone in a yield of 51% of theory. See EP-A1 949,243, Example 6–3.

A disadvantage of this process is the use of a large amount of auxiliaries, e.g., buffer salts that hinder work-up, lead to a considerable salt content in the wastewater and, following their removal, give rise to high costs for an environmentally-friendly disposal.

Also known is a process for the preparation of mono (fluoroalkyl)-acetophenones in which the process of EP-A1 949,243 is modified inasmuch as the process is carried out in the presence of halide ions, e.g., in the presence of hydrochloric acid, and without the addition of buffer salts (DE 197 19 054 A1). The above-mentioned disadvantages then do not arise. However, the transference of this process to the preparation of poly(fluoroalkyl)acetophenones has not been obvious because the poly-(fluoroalkyl) anilines that would then be required as starting materials are weaker bases than mono(fluoroalkyl)anilines and therefore tend to form triazenes. A reworking of the process according to DE 197 19 054 A1 using bis-3,5-(trifluoromethyl)aniline as starting material gave bis-3,5-(trifluoromethyl) acetophenone in a yield of only 33% (see Example 3). An increase in the amount of hydrochloric acid did not lead to an improvement in the yield.

There is therefore still a need for a simple and cost-effective process for the preparation of acetophenones which are di- or poly-substituted by fluoroalkyl groups on the aromatic ring that can be carried out on an industrial scale.

A process has now been found for preparing acetophenones that are di- or polysubstituted by fluoroalkyl groups on the aromatic ring from corresponding fluoroalkylanilines and acetaldoxime.

SUMMARY OF THE INVENTION

The present invention accordingly relates to a process for the preparation of acetophenones that are di- or polysubstituted by fluoroalkyl groups on the aromatic ring comprising (a) preparing a diazonium salt mixture from the corresponding fluoroalkylaniline, (b) reacting the diazonium salt mixture with acetaldoxime at 5 to 50° C. in the presence of halide ions, at least one strong acid that is not a hydrohalic acid, and at least one copper and/or palladium compound and in the absence of buffer salts and reducing agents, and (c) heating the mixture from step (b) to a temperature in the range 70 to 160° C.

DETAILED DESCRIPTION OF THE INVENTION

In the process according to the invention it is possible, for example, to use fluoroalkylanilines of the formula (I)

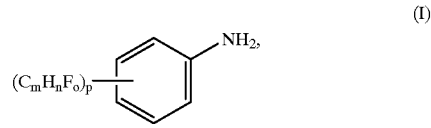

wherein
m is an integer from 1 to 4,
n is zero or an integer from 1 to 2 m,
o is an integer from 1 to 2 m+1, and
p is an integer from 2 to 4,
with the proviso that n+o=2 m+1.

In formula (I) the $C_mH_nF_o$ radicals present can be identical or different but are preferably identical.

In the formula (I) m is preferably 1 or 2 (particularly preferably 1), n is preferably zero, o is preferably 2 m+1, and p is preferably 2.

If, in the formula (I), p is 2, then both $C_mH_nF_o$ groups are preferably arranged in the meta position relative to the $NH_2$ group. If, in the formula (I), p is 3 or 4, then two of the $C_mH_nF_o$ groups are preferably arranged in the meta position relative to the $NH_2$ group.

Particular preference is given to using bis-3,5-(trifluoromethyl)-aniline as compound of the formula (I).

It is an essential feature of the present invention that the reaction with acetaldoxime is carried out in the presence of halide ions and at least one strong acid that is not a hydrohalic acid. Examples of such suitable strong acids are sulfuric acid, perchloric acid, alkyl- and arylsulfonic acids, and strong carboxylic acids. Alkylsulfonic acids can contain, for example, 1 to 6 carbon atoms and can be optionally substituted by halogen atoms. Arylsulfonic acids can contain, for example, 6 to 10 carbon atoms and can be optionally substituted by halogen atoms. The strong carboxylic acids may, for example, be alkanecarboxylic acids containing 2 to 6 carbon atoms substituted by halogen atoms. Individual examples of sulfonic acids and strong carboxylic acids are methanesulfonic acid, trifluoromethane-sulfonic acid, trichloroacetic acid, and trifluoroacetic acid. Preference is given to using sulfuric acid or mixtures of sulfuric acid and one or more other strong acids different from hydrohalic acids. Particular preference is given to using sulfuric acid.

The procedure may involve, for example, carrying out the reaction of the fluoroalkylaniline with sodium nitrite in the presence of a hydrohalic acid and at least one strong acid that is not a hydrohalic acid. The acids are preferably used as concentrated aqueous solutions, for example, hydrochloric acid having a concentration in the range 25 to 40% by weight, hydrobromic acid having a concentration in the range 25 to 70% by weight, and sulfuric acid having a concentration in the range 35 to 100% by weight. Instead of hydrochloric acid or hydrobromic acid, it is also possible to introduce hydrogen chloride gas or hydrogen bromide gas into the reaction mixture.

Preference is given to using a mixture of hydrohalic acid, particularly hydrochloric acid, and sulfuric acid. The molar ratio of such hydrohalic/sulfuric acid mixtures can, for example, be in the range 1:2 to 4:1.

Based on 1 mol of fluoroalkylaniline, it is possible, for example, to use 5 to 9 equivalents of protons in the form of hydrohalic acid and at least one strong acid that is not a hydrohalic acid. This amount is preferably 5.5 to 6 equivalents.

The water content of the reaction mixture for the preparation of the diazonium salt mixture can, for example, be 45 to 80% by weight.

The diazonium salt mixture can be prepared by initially introducing the acids and water, adding the fluoroalkylaniline, then slowly adding an aqueous sodium nitrite solution at, for example, −20 to 0° C., and allowing the mixture to react fully.

It is a further essential feature of the present invention that no buffer salts (e.g., no sodium acetate) are added to the prepared diazonium salt mixture.

For the reaction with acetaldoxime it is possible, based on 1 mol of fluoroalkylaniline, to use, for example, 1 to 4 mol of acetaldoxime (preferably 1.2 to 3.2 mol).

Examples of suitable copper compounds are salts and complex compounds of copper in which copper is present in the +1 or +2 oxidation states.

Examples of copper salts are copper halides, copper sulfates, copper nitrates, copper tetrafluoroborates, and copper salts of organic acids, such as alkyl- and arylcarboxylic acids. Examples of complex compounds of copper are those with hydroxylamine or acetaldoxime ligands. Mention may be made specifically of copper(II) sulfate, copper(II) sulfate pentahydrate, copper(I) chloride, copper(II) chloride, copper(II) chloride dihydrate, copper(I) bromide, copper(II) bromide, copper(II) acetate, copper(II) acetate hydrate, copper(II) fluoride, copper(II) fluoride trihydrate, copper(II) formate hydrate, copper(II) hydroxide, copper(II) hydroxide carbonate, copper(II) nitrate, copper(II) nitrate hydrate, copper(II) nitrate hemipentahydrate, copper(II) tetrafluoroborate, and $Cu(O-N=CH-CH_3)_n$ where n is 1 or 2.

Examples of suitable palladium compounds are salts and complex compounds of palladium in which palladium is present in the +2 oxidation state. Examples of palladium salts are palladium halides, palladium sulfate, palladium nitrate, and palladium salts of organic acids, such as alkyl- and arylcarboxylic acids. Examples of complex compounds of palladium are those containing amine, ethylenediamine, tetramethylene-diamine, acetylacetonate, or phosphine ligands. Mention may be made specifically of: palladium(II) acetate, propionate, chloride, nitrate, sulfate, and trifluoroacetate.

It is also possible to use mixtures of copper compounds, mixtures of palladium compounds, or mixtures of copper and palladium compounds. Preference is given to using copper compounds, particularly preferably copper(II) halides or copper(II) sulfate, which may or may not contain water of crystallization.

Based on 1 mol of fluoroalkylaniline used, it is possible to use, for example, 0.01 to 0.2 mol (preferably 0.04 to 0.12 mol) of copper and/or palladium compounds.

It is a further essential feature of the present invention that no buffer salts (such as sodium acetate) and no reducing agent (such as sodium thiosulfate) are added before and/or during the reaction of the diazonium salt mixture with the acetaldoxime.

The reaction with the acetaldoxime is preferably carried out at 5 to 40° C., particularly at 10 to 30° C.

The presence of halide ions during the reaction with acetaldoxime, as required according to the invention, can be achieved in the simplest case by (co-)using a hydrohalic acid as acid for the preparation of the diazonium salt mixture, for example, 25 to 40% strength by weight aqueous hydrochloric acid or 25 to 70% strength by weight aqueous hydrobromic acid. If, in the preparation of the diazonium salt mixture, only acids other than hydrohalic acids have been used, halide ions must be added, for example, in the form of alkali metal halides or alkaline earth metal halides such as sodium chloride or sodium bromide.

The reaction mixture for the reaction with the acetaldoxime can contain, for example, 1 to 50 mol (preferably 1.5 to 35 mol) of halide ions, based on 1 mol of copper and/or palladium compounds. If the diazonium salt mixture does not bring sufficient halide ions with it, the halide ions must be added separately.

The reaction with the acetaldoxime is preferably carried out by initially introducing the copper and/or palladium compounds, water, and acetaldoxime, and slowly metering in the aqueous diazonium salt mixture. It is advantageous to ensure intensive thorough mixing of the reaction mixture during the metered addition of the diazonium salt mixture, for example, by vigorous stirring or by means of a vibration mixer or a dispersion device, such as the Ultra-Turrax® type.

It is also advantageous, in the preparation of the components to be reacted with one another, to largely exclude the presence of oxygen during the reaction. For this purpose, it is possible, for example, to work in an inert gas atmosphere, to introduce inert gas into the components and/or reaction mixtures to be handled, or to apply a gentle vacuum for degassing.

When the addition of the diazonium salt mixture and of the acetaldoxime is complete, the reaction mixture can be left to react, if required, for some time, for example, for 15 minutes to 1 hour at temperatures, for example, in the range 20 to 50° C. Treatment with (further) hydrochloric acid prior to work-up is not required.

For work-up, the fully reacted reaction mixture is heat-treated according to the invention at elevated temperature, heating being carried out to 70 to 160° C. (preferably to 70 to 110° C.), optionally under pressure, and the mixture is maintained in this temperature range, for example, for 15 minutes to 12 hours (preferably 1 to 4 hours). To isolate the crude product, during the heat treatment or subsequently, the fully reacted reaction mixture can be worked up by steam distillation or azeotropic distillation. Alternatively, the fully reacted reaction mixture can, following the heat treatment, be cooled to, for example, 0 to 70° C., and the crude product can be isolated by phase separation, extraction, or, for solid products, filtration.

The crude acetophenones that are di- or polysubstituted by fluoroalkyl groups on the ring that are present following work-up, e.g., by steam distillation, phase separation, extraction, or filtration, can, if required, be further purified, e.g., by fractional distillation over a column.

In the manner according to the invention, the desired products can be obtained in purities of generally greater than 98% and in yields of generally 50 to 58% of theory.

The use of a fluoroalkylaniline of the formula (I) gives the corresponding acetophenone of the formula (II)

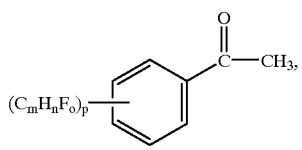
(II)

in which the symbols used have the meanings given for formula (I).

Although the process according to the invention, in contrast to the prior art, is realized without the addition of buffer salts and reducing agent and can be carried out with smaller amounts of strong inorganic acids and copper compounds, the yield of target products is generally increased (relatively) by at least 20%. This is particularly surprising and makes the process according to the invention significantly more efficient than the known processes. The amounts of wastewater and the salt contents thereof are significantly lower, and the space-time yield is considerably increased. The reaction temperature according to the invention, which is elevated compared with the prior art, suggested that an increase in decomposition reactions might occur but such decomposition surprisingly does not occur.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

274 g of water, 171 g of 30% strength by weight aqueous hydrochloric acid, and 69 g of 98% strength by weight aqueous sulfuric acid were initially introduced and cooled to −5° C. 115 g of bis-3,5-(trifluoromethyl) aniline with a content of 99% were then metered in at this temperature. 35.6 g of sodium nitrite were then dissolved in 110 g of water and metered into this solution over the course of one hour at 0° C., and the mixture was then stirred for 1 hour. An initial charge was prepared from 5.8 g of copper(II) sulfate pentahydrate, 172 g of water, and 44.4 g of acetaldoxime and heated to 20° C. The diazonium salt solution prepared above was metered into this initial charge with vigorous stirring over the course of 2 hours, and then the mixture was left to afterreact for 30 minutes at 30° C. The mixture was then heated to 100° C. over the course of 2 hours and then stirred for 3 hours at this temperature. After cooling to 50° C., the phases were separated. The organic phase was distilled over a column, giving 71.1 g of bis-3,5-(trifluoromethyl) acetophenone (99% pure according to GC). This corresponds to a yield of 55% of theory.

Example 2

A diazonium salt solution was prepared as described in Example 1.

An initial charge was prepared from 8.7 g of copper(II) sulfate pentahydrate, 172 g of water, 100 g of toluene, and 44.4 g of acetaldoxime and cooled to 10° C., and the diazonium salt solution was then added dropwise over the course of 1.5 hours. The mixture was then heated to 100° C. and stirred for 3 hours at this temperature. Following cooling to 50° C., the phases were separated. The organic phase was distilled over a column, giving 64.6 g of bis-3,5-(trifluoromethyl)acetophenone (99% pure according to GC). This corresponds to a yield of 50% of theory.

Example 3 (comparison)

(Procedure in accordance with DE 197 19 054 A1, that is, only with hydrochloric acid)

254 g of water and 133 g of aqueous 30% strength by weight of hydrochloric acid were initially introduced and cooled to −5° C. 57.3 g of bis-3,5-(trifluoromethyl)aniline with a content of 99% were then added dropwise at this temperature. 18.3 g of sodium nitrite were then dissolved in 54.8 g of water and were metered into the bis- 3,5-(trifluoromethyl)-aniline-containing mixture over the course of one hour at 0° C., and the mixture was further stirred for one hour. An initial charge was prepared from 2.9 g of copper(II) sulfate pentahydrate, 86.2 g of water, and 22.2 g of acetaldoxime and vigorously stirred at 25° C. The previously prepared diazonium salt solution was metered in over the course of 2 hours, and the mixture was left to afterreact for 30 minutes at 30° C. The mixture was heated to 100° C. over the course of 2 hours and then stirred for 3 hours at this temperature. After cooling to 50° C., the phases were separated. The organic phase was distilled over a column, giving 21.3 g of bis-3,5-(trifluoromethyl) acetophenone (content according to GC 99%). This corresponds to a yield of 33% of theory.

What is claimed is:

1. A process for the preparation of acetophenones that are di- or polysubstituted by fluoroalkyl groups on the aromatic ring comprising (a) preparing a diazonium salt mixture from the corresponding fluoroalkylaniline in the presence of a hydrohalic acid and at least one strong acid that is not a hydrohalic acid, (b) reacting the diazonium salt mixture with acetaldoxime at 5 to 50° C. in the presence of halide ions, at least one strong acid that is not a hydrohalic acid, and at least one copper and/or palladium compound and in the absence of buffer salts and reducing agents, and (c) heating the mixture from step (b) to a temperature in the range 70 to 160° C.

2. A process according to claim 1 wherein a fluoroalkylaniline of formula (I)

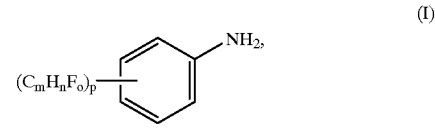
(I)

wherein m is an integer from 1 to 4, n is zero or an integer from 1 to 2 m, o is an integer from 1 to 2 m +1, and p is an integer from 2 to 4, with the proviso that n+o=2 m+1, is used to prepare an acetophenone of formula (II)

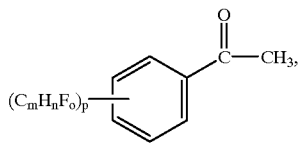

(II)

wherein m, n, o, and p have the meanings given for formula (I).

3. A process according to claim 2 wherein in formulas (I) and (II) m is 1 or 2, n is zero, o is 2 m+1, and p is 2.

4. A process according to claim 1 wherein a mixture of hydrochloric acid and sulfuric acid is used in step (b).

5. A process according to claim 1 wherein 1 to 4 mol of the acetaldoxime and 0.01 to 0.2 mol of the copper and/or palladium compound are used per mole of fluoroalkylaniline.

6. A process according to claim 1 wherein the reaction of the diazonium salt mixture with acetaldoxime is carried out at 5 to 40° C.

7. A process according to claim 1 wherein 1 to 50 mol of halide ions are used per 1 mol of the copper and/or palladium compound.

8. A process according to claim 1 wherein the presence of oxygen is largely excluded during the preparation of the components to be reacted with one another.

9. A process according to claim 1 wherein heating step (c) is carried out at 70 to 160° C. for from 15 minutes to 12 hours.

10. A process according to claim 1 wherein a copper compound is used in step (b).

11. A process according to claim 1 wherein the diazonium salt mixture in step (a) is carried out in the presence of a hydrohalic acid and sulfuric acid.

12. A process according to claim 1 wherein the step (a) the hydrohalic acid and the strong acid that is not a hydrohalic acid together provide 5 to 9 equivalents of protons per 1 mol of fluoroalkylaniline.

* * * * *